United States Patent [19]
Firth et al.

[11] Patent Number: 5,356,392
[45] Date of Patent: Oct. 18, 1994

[54] SHIELDED BLOOD COLLECTION TUBE HOLDER

[75] Inventors: John R. Firth, Wilsonville, Oreg.; Anthony R. Perez, Alhambra, Calif.

[73] Assignee: Safety Syringes, Inc., Arcadia, Calif.

[21] Appl. No.: 183,605

[22] Filed: Jan. 18, 1994

Related U.S. Application Data

[63] Continuation-in-part of Ser. No. 783,825, Oct. 29, 1991, Pat. No. 5,279,581, which is a continuation-in-part of Ser. No. 581,734, Sep. 12, 1990, Pat. No. 5,108,378, which is a continuation-in-part of Ser. No. 521,243, May 9, 1990, abandoned.

[51] Int. Cl.$^5$ .............................................. A61M 5/32
[52] U.S. Cl. ..................................... 604/198; 128/763
[58] Field of Search ............... 604/198, 263, 110, 187, 604/192; 128/763–765, 760

[56] References Cited

U.S. PATENT DOCUMENTS

| | | | |
|---|---|---|---|
| 5,070,884 | 12/1991 | Columbus et al. | 128/763 X |
| 5,070,885 | 12/1991 | Bonaldo | 128/763 |
| 5,120,311 | 6/1992 | Sagstetter et al. | 604/198 X |
| 5,131,405 | 7/1992 | Burns | 128/763 |
| 5,259,841 | 11/1993 | Hohendorf et al. | 604/198 X |

Primary Examiner—John D. Yasko
Attorney, Agent, or Firm—Lyon & Lyon

[57] ABSTRACT

There is disclosed herein a blood collection tube holder having a body and a protector case, and preferably with a dedicated needle attached to the body. The tube holder is molded of plastic or other suitable material which is sterilizable. The device comprises five parts including the body, protector case, needle, needle protective cap, and a needle boot. The protector case is mounted over the body, and the needle is attached to the body and extends through an opening in the protector case. The needle is covered by the needle protective cap which is removably attached to a needle hub on the end of the body. The needle protective cap is removed for use, and after use the protector case is moved with respect to the body until detents engage openings to thereby lock the protector case in a position shielding the needle. The construction of the holder is such that the practitioner can hold the protector case against the arm of a patient with the index finger and draw the body of the holder rearward with the thumb and forefinger, thereby enabling use with one hand.

12 Claims, 8 Drawing Sheets

SHIELDED BLOOD COLLECTION TUBE HOLDER

This is a continuation-in-part of application Ser. No. 07/783,825 filed on Oct. 29, 1991 now U.S. Pat. No. 5,279,581 which is a continuation in part of Ser. No. 581,734 filed on Sep. 12, 1990, now U.S. Pat. No. 5,108,378 which was a continuation in part of application Ser. No. 07/521,243, now abandoned, filed on May 9, 1990.

BACKGROUND OF THE INVENTION

The rapid spread of AIDS has generated a rapid development of methods for preventing the spread of communicable diseases from the inadvertent reuse of needle devices, accidental needlestick injuries suffered by medical and dental practitioners, and ineffective sterilization of reusable devices. To be effective, the devices employed must be simple to manufacture and easy to use. U.S. Pat. No. 5,108,378 discloses a syringe having a rectangular body cross-section which permits the use of a protector case of matching interior cross section. Continuation-in-part application 07/783,825 describes three devices which apply features of the above patent. The present application describes the incorporation of many of the features of the above patent and CIP application to the design of a shielded blood collection tube holder of the type in common use by phlebotomists and other medical practitioners in the procedure for obtaining multiple blood samples for analysis. A sterilized, single use, shieldable device for use in blood collection will extend the benefits of the self-shielded, disposable safety syringe to this application.

Examples of disclosures in United States Patents are as follows:

U.S. Pat. No. 4,643,199 discloses a sterile barrel and piston assembly with the barrel being twisted to lock it in place over the needle. The twisting action requires two hand operation of the device and the number of components render the device expensive to manufacture.

U.S. Pat. No. 4,813,426 discloses an outer barrel with a needle carrier mounted within the sleeve and movable axially within the sleeve. The needle carrier is positioned and locked by means of a position control button on the carrier and a slot in the outer barrel. Retraction of the needle may be initiated with one hand but is not easily accomplished unless the spring actuated retraction feature is utilized. Use of the retraction spring presents control problems with the rate of retraction and shelf life restraints due to fatigue of the spring.

U.S. Pat. No. 4,871,355 discloses an inner and outer tube with locking means to prevent the outer tube from becoming disengaged. The device is a reusable device having a means described of inserting a needle sheath into the end of the shield to cover the forward end of the needle and to unscrew and dispose of the needle. This presents the exposure of the rearward end of the contaminated needle during the disposal operation.

U.S. Pat. No. 4,892,523 discloses a disposable device with an inner and outer sleeve with various means of locking the sleeves relative to each other. The various systems require two handed operation to position the locking mechanisms.

U.S. Pat. No. 5,059,185 discloses an inner and outer cylinder with axial slits in the outer cylinder to permit the shield to move along the ramped outer wall of the inner cylinder. The device requires two hands to operate effectively due to the design of the detent mechanism.

U.S. Pat. No. 5,067,945 discloses an inner and outer cylindrical tube having interacting rings and grooves for securing the cylinders relative to each other. A ring has been added to the outside of the outer cylinder to facilitate one handed operation, however this cannot be accomplished with patient comfort unless the needle is previously removed from the patient.

There still exists a need for a blood collection tube holder which provides ease of one handed operation, assured sterility, and economical manufacture.

SUMMARY OF THE INVENTION

The present invention relates to a blood collection tube holder with a body and a protector case, and preferably a dedicated needle attached to the body. The tube holder is molded of plastic or other suitable material which is sterilizable. The device comprises five parts including the body, protector case, needle, needle protective cap, and needle boot.

The protector case is assembled with the case retracted over the body and the needle attached to the body and extending through an opening in the protector case. The needle is covered by the needle protective cap which is removably attached to a needle hub on the end of the body.

The device is packaged in a sealed container and sterilized.

The user removes the device from the package and the needle protective cap is then removed and the device is ready for use. The needle is inserted into the blood vessel of the patient and an evacuated blood collection tube is inserted into the open end of the blood collection tube holder and over the interior end of the needle. The vacuum in the blood collection tube draws blood into the tube from the blood vessel. When the desired amount of blood has been withdrawn, the tube is removed. This process is repeated until the required number of samples have been obtained.

When the last sample tube has been removed from the holder, the practitioner holds the protector case against the arm of the patient with the index finger and draws the body of the holder rearward with the thumb and third finger. This action withdraws the needle from the blood vessel of the patient and into the protector case. The body is retracted until detents at the ends of arms of the protector case engage slots in the body and lock the protector case in a shielded position. In this position the needle is covered obviating the need to recap the needle and protecting those handling the device during disposal. Since the device is not reused there is no need to remove the contaminated needle nor to autoclave or otherwise resterilize the device.

The benefits of the invention are several, including the following:

1. The device is sterilized after packaging and used only once, ensuring the maximum protection for the patient.
2. The device is provided with a dedicated needle and is received in a ready to use configuration eliminating any assembly prior to use.
3. The protector case and single use/disposable nature of the device make it unnecessary to recap or remove the needle from the holder eliminating exposure to the contaminated needle.

4. The dedicated needle and individual sterile packaging reduce the number of component parts and favorably impact manufacturing costs.

DETAILED DESCRIPTION OF THE PREFERRED EMBODIMENT

Figure 1A:
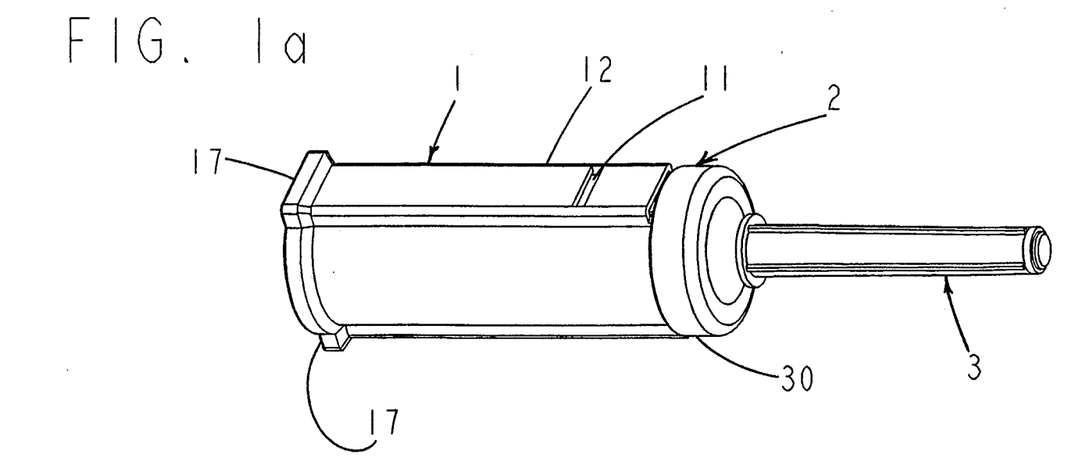
FIG. 1a & 1b are perspective views of a blood collection tube holder of the present invention, as removed from a sterile package, with a needle protective cap in place and a protector case in an unguarded position.
Figure 1B:
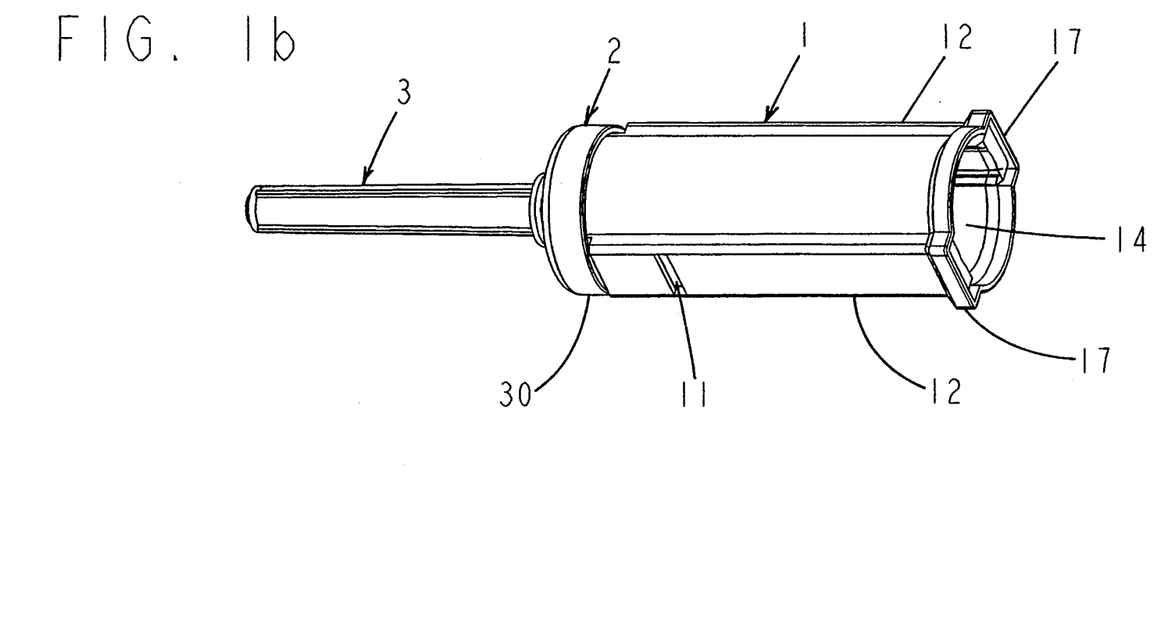
Figure 2A:
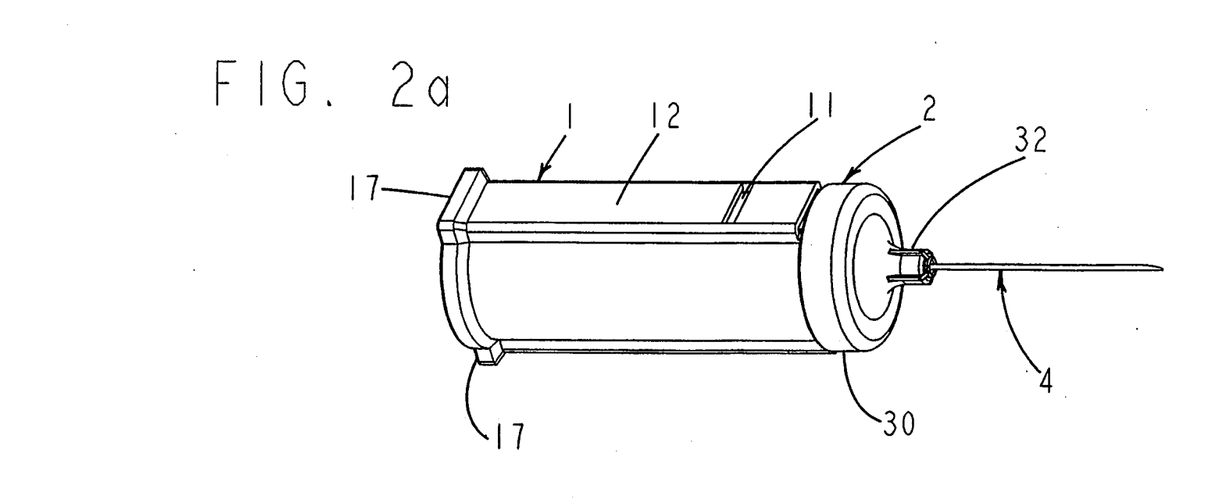
FIG. 2a & 2b are perspective views of the holder, ready for the needle to be inserted into the patients blood vessel, with the protector case in the unguarded position and the needle protective cap removed, ready for use.
Figure 2B:
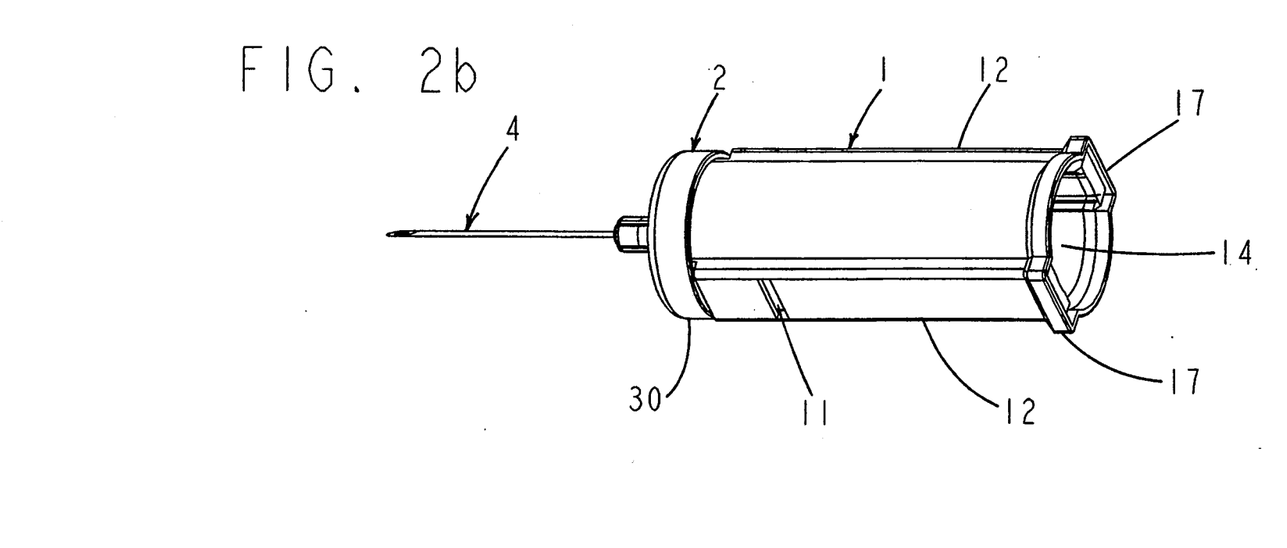
Figure 3A:
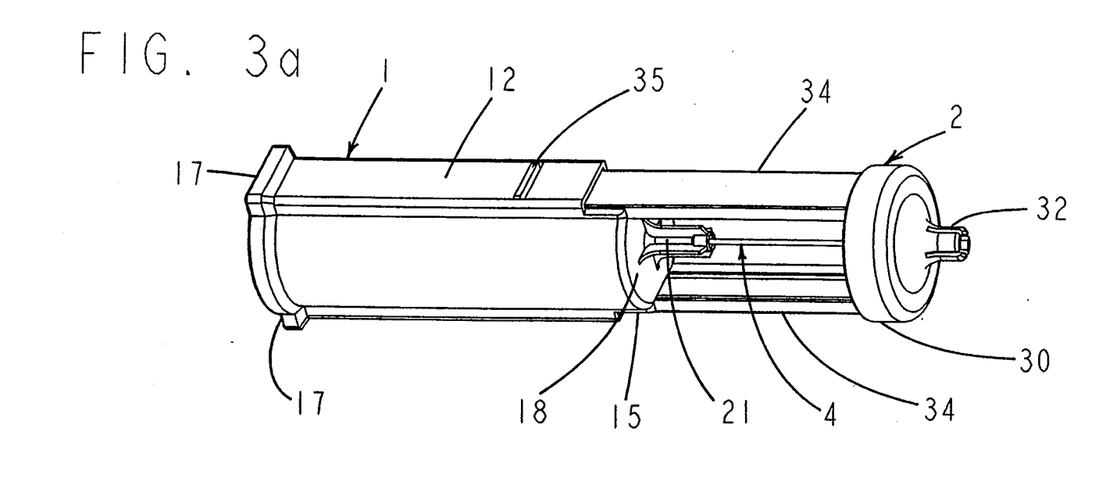
FIG. 3a & 3b are perspective views of the holder, after removal of the needle from the patient, with the protector case in an extended (guarded) position ready for disposal after use.
Figure 3B:
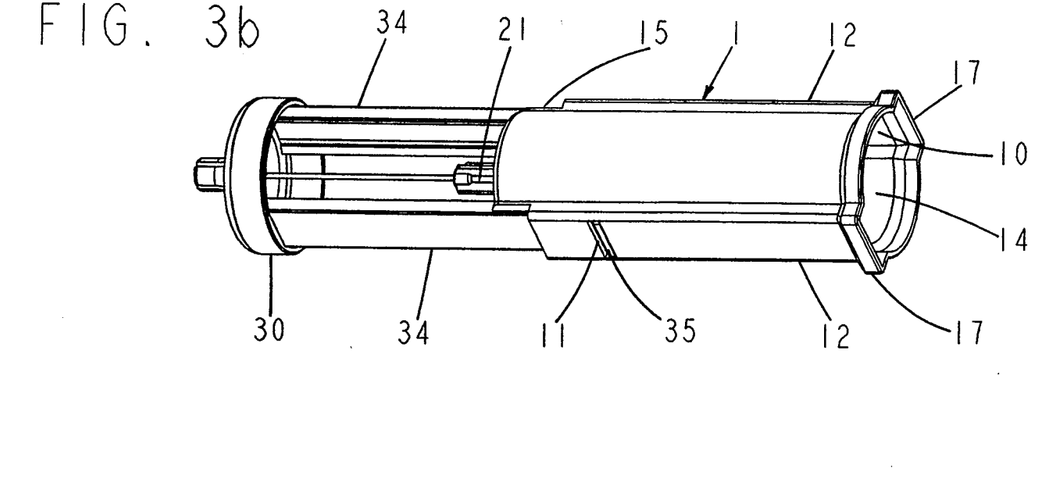
Figure 4A:
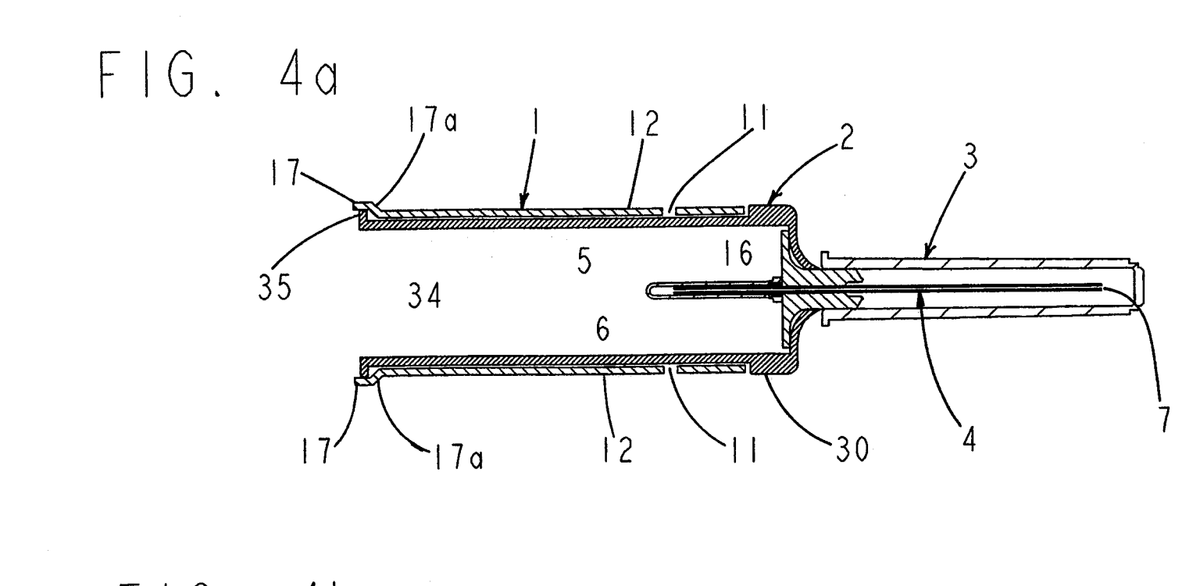
FIG. 4a is an axial section through the holder assembly in the plane of the center of detent arms of the protector case taken along lines 4A—4A of FIG. 4b.
Figure 4B:
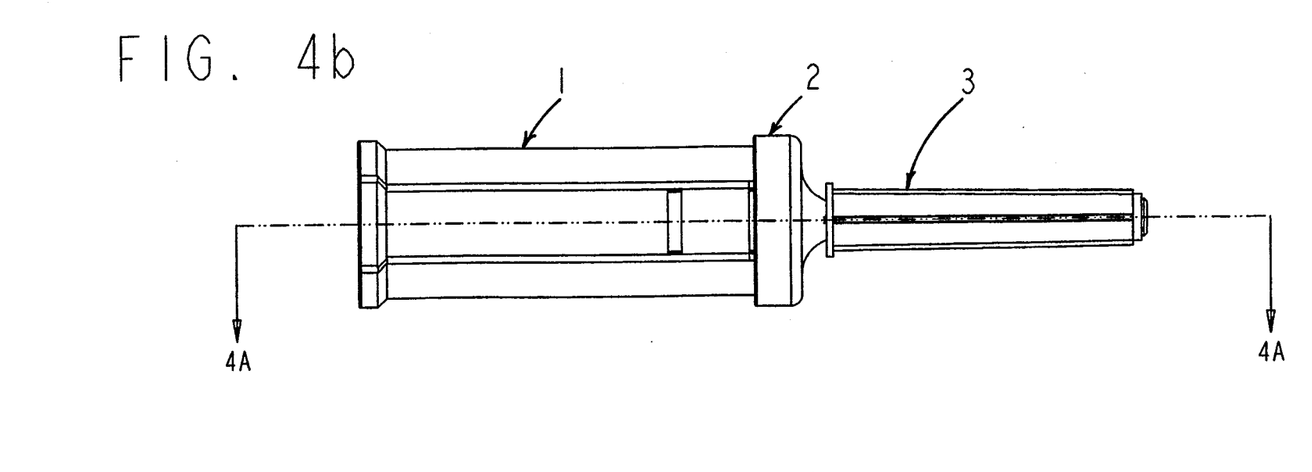

Turning now to the drawings, and first to FIGS. 1–4, FIG. 1 depicts the device as it appears after it is removed from the sterile unit packaging. The protector case 2 is retracted into the body 1 with the needle protective cap 3 in place over the needle 4 (FIG. 2). FIG. 2 shows the device, ready to be used, with the needle protective cap 3 (FIG. 1) removed and the protector case 2 still in the retracted (unguarded) position to expose the needle 4. FIG. 3 shows the device after use, ready for disposal, with the protector case 2 now moved to the forward (guarded) position over the needle 4. FIG. 4 shows a section through the device of FIG. 1. A needle boot 5 covers an inside end 6 of the needle 4 and attaches to a needle boot hub 16 (FIG. 4 & 5c). An outside end 7 of the needle 4 is covered by the needle protective cap 3.

Figure 5A:
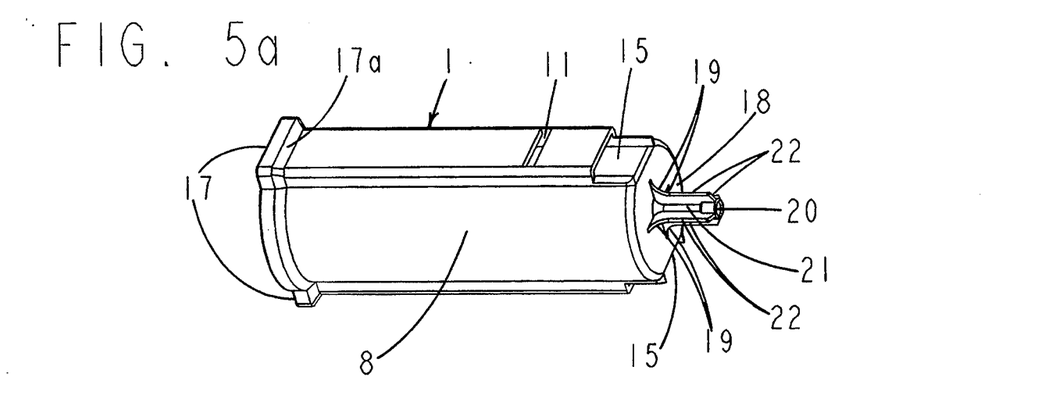
FIGS. 5a & 5b are perspective views of the body.
Figure 5B:
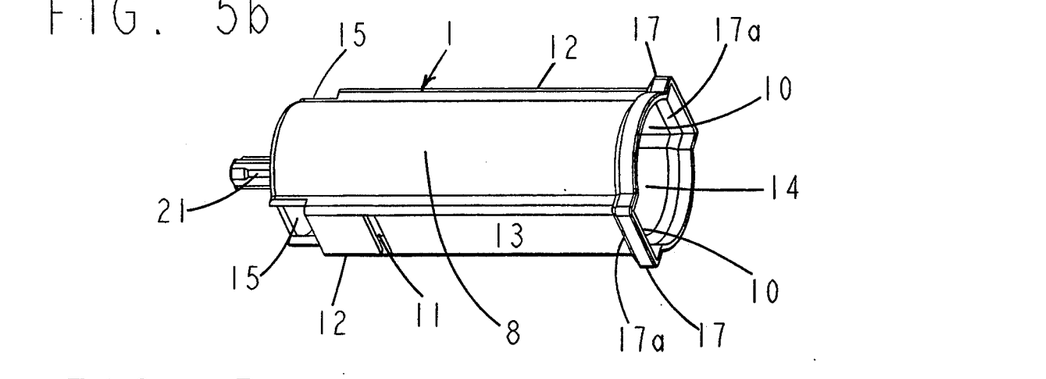
Figure 5C:
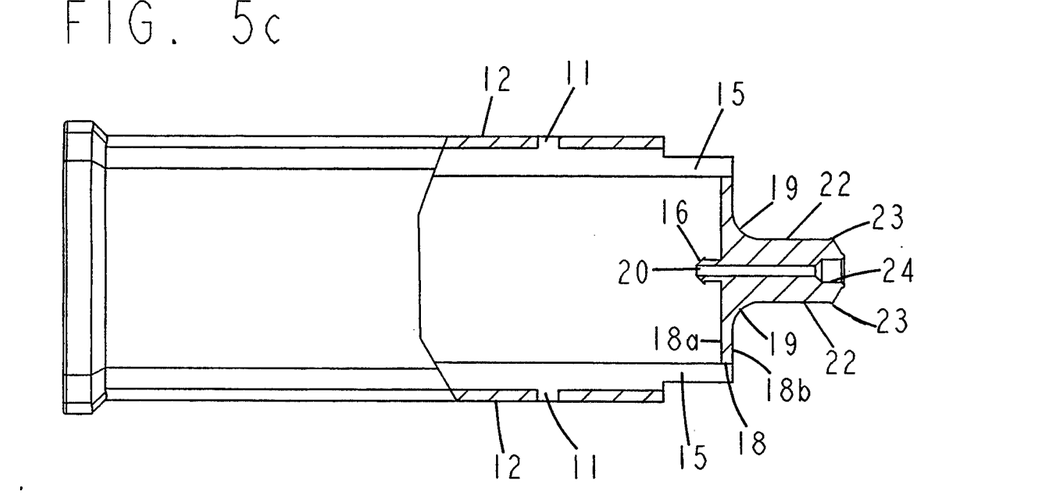
FIG. 5c is an enlarged elevation view of the body with a partial section through the body at the needle hub end.
Figure 6A:
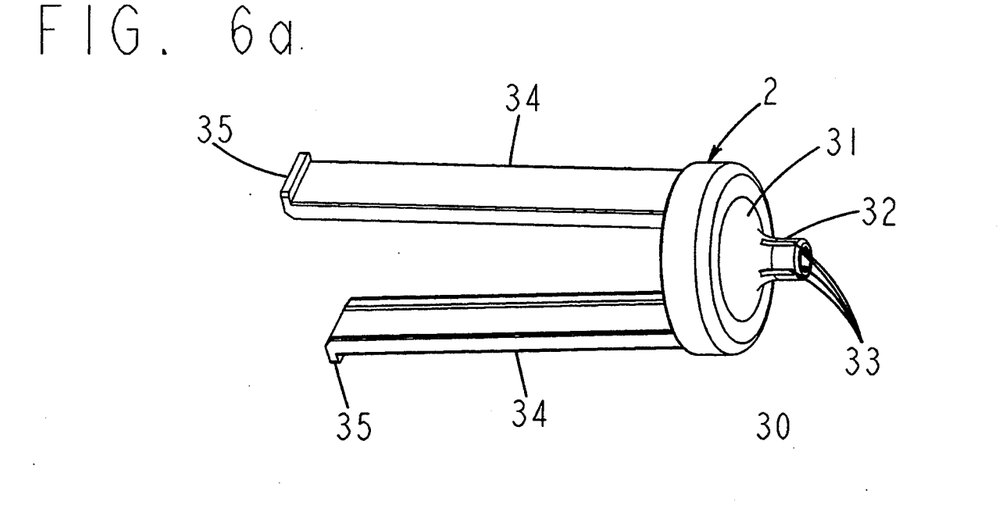
FIGS. 6a & 6b are perspective views of the protector case.
Figure 6B:
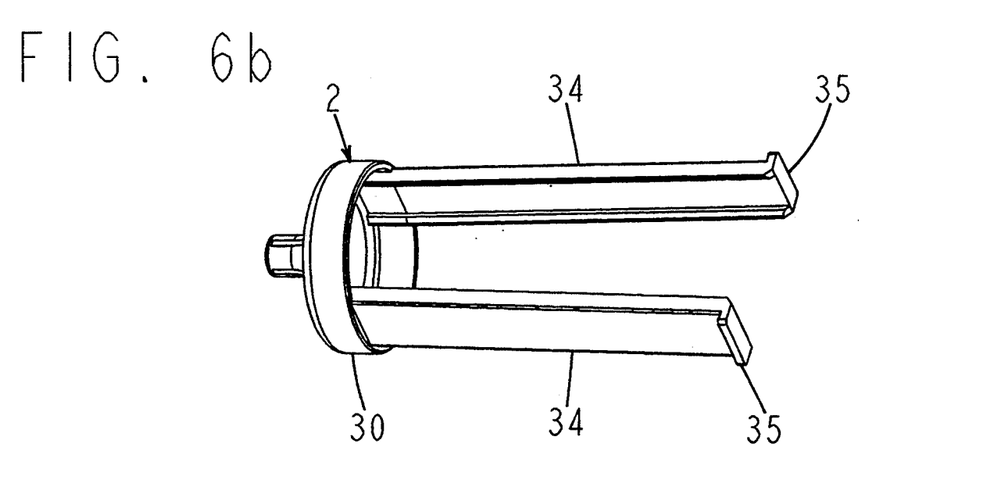

Referring particularly to FIGS. 5a, 5b, & 5c, the body 1 of the device is substantially cylindrical in shape having a cylinder wall 8 with two axially extending channels 10 molded into the cylinder wall 8 of the body 1 diagonally opposite each other. Two slots 11 are formed into the channel walls 12 at a distance 13 from the open end of the body cavity 14. These slots 11 define the forward travel of the protector case 2 (FIG. 3) to the guarded position. Two windows 15 are located in the channel walls 12 at the closed end of the body 1. These windows 15 permit the molding of the boot hub 16 (FIG. 5c) in the interior of the body 1 and the insertion of the protector case detent arms 34 (FIG. 6) during assembly. At the open end of the body cavity 14, the body 1 and channel walls 12 have an outward flare 17 to provide additional rigidity to the body 1 and to releasably house detent tabs 35 (FIG. 3 & 6) of the protector case detent arms 34 (FIG. 6). The flared area 17 has a sloped, transition section 17a which provides a ramp to flex the detent arms 34 inwardly to release the detent tabs 35 as the protector case 2 is moved forward.

At the closed (needle end) of the body 1 there is an end wall 18 (FIG. 5c). A boot hub 16 is integrally molded to the interior side 18a of the end wall 18. On the forward surface 18b of the end wall 18, four needle hub support vanes 19 are attached and extend radially outward from a needle opening 20 and axially forward to the end of the needle hub 21. The needle hub support vanes 19 have forward edges 22 parallel to the longitudinal axis of the body 1. These edges 22 interact with the needle protective cap 3 (FIG. 8c) with the forward edges 22 engaging the interior surface 43 (FIG. 8c) of the needle protective cap 3 to secure the needle protective cap 3 to the body 1. To further secure the needle protective cap 3 to the needle hub support vanes 19 there is a small radial protrusion 23 on the forward end of each forward edge 22 which has an interference fit with the interior bore 43 (FIG. 8c) of the needle protective cap 3.

There is a needle opening 20 extending through the needle hub 21, wall 18, and boot hub 16. The needle hub 21 contains an adhesive pocket 24 which extends axially into the hub. The needle 4 is attached so that it extends through the needle opening 20 with the interior end 6 (FIG. 4a) extending through the end wall 18, the boot hub 16, and into the body cavity 14. The structure of the end wall 18, support vanes 19, and needle hub 21 are specifically designed to minimize the plastic volume in this area to improve heat transfer and manufacturing cycle times.

Figure 6C:
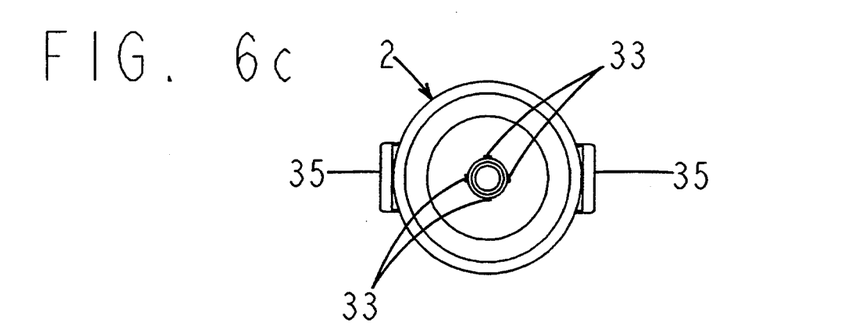
FIGS. 6c is an end elevation of the protector case.

Referring to FIGS. 6a, 6b and 6c the protector case 2 has a short cylindrical section 30 with one end substantially closed by a conical wall 31. This conical wall 31 joins to a guard cylinder 32 which has four slots 33 cut radially through its surface at ninety degree intervals and running axially from the outside end of the guard cylinder 32 through the conical wall 31. These slots 33 permit the forward edges 22 of the hub support vanes 19 to pass through the wall of the guard cylinder 32 to engage the inner surface 43 of the needle cap 3 and thereby attach the needle cap 3 to the body 1. The protector case has two detent arms 34 integrally molded to the short cylindrical section 30 and projecting rearward away from the conical wall 31. These detent arms 34 are angled slightly outwardly from the axis of the protector case 2 to provide outward pressure on the detent arms when they are contained in the channels 10 of the body 1. Detent tabs 35, extending at right angles to the detent arms 34, are integrally molded to the outside surfaces of the detent arms 34 at the end opposite the concave conical wall 31. When the protector case 2 is slid forward, the detent tabs 35 are forced inward by the sloped surface of the outward flare 17 of the body 1 and flex the detent arms 34 inwardly. The detent tabs 35 slide forward in the channels 10 until they reach the slots 11 in the channel walls 12. The outward pressure of the detent arms 34 forces the detent tabs 35 into the slots 11 and prevents further movement of the protector case 2 in either direction, forward, backward and rotationally relative to the body 1. In this position, the guard cylinder 32 covers the outer end of the needle 4 and shields the practitioner from accidental needlestick injury.

Figure 7:
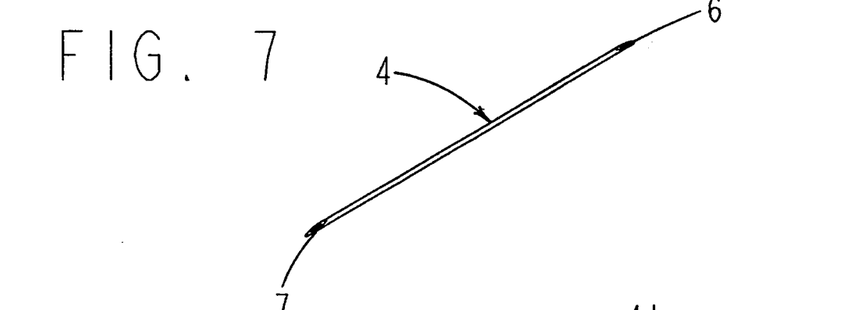
FIG. 7 is a perspective view of the needle.
Figure 10:
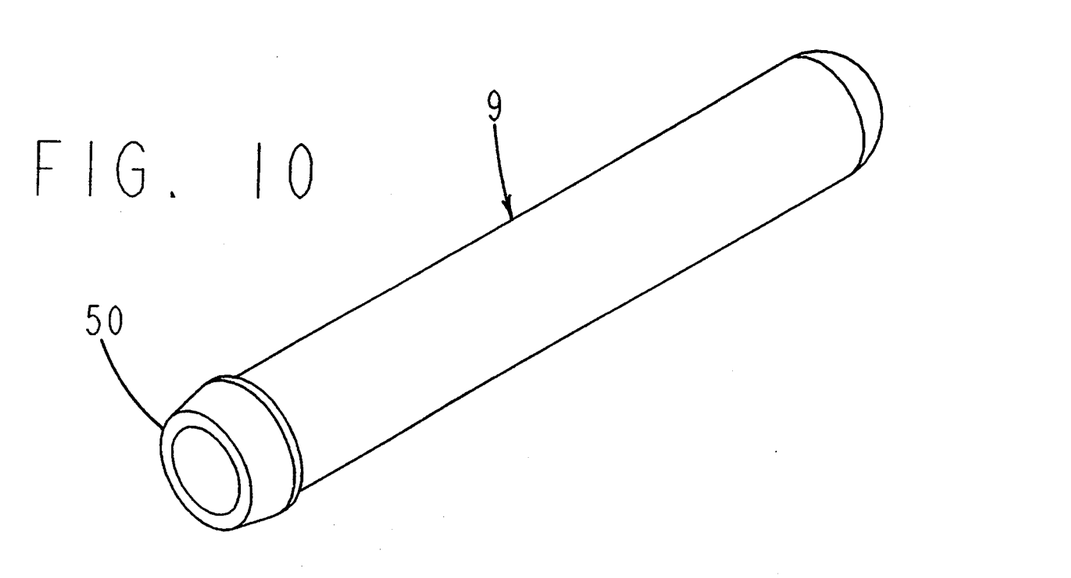
FIG. 10 is a perspective view of the blood collection tube.

As shown in FIG. 7, the needle 4 is a metal cannula, having a hollow passageway through its length for the passage of fluids. The forward end 7 is sharpened to permit penetration of the patients tissue and the rearward end 6 is sharpened to permit penetration of the rubber membrane of the needle boot 5 (FIG. 4) and the rubber stopper 50 of a conventional blood collection tube 9 (FIG. 10). The needle 4 is affixed to the needle hub 21 by adhesive in the manufacturing process.

Figure 8A:
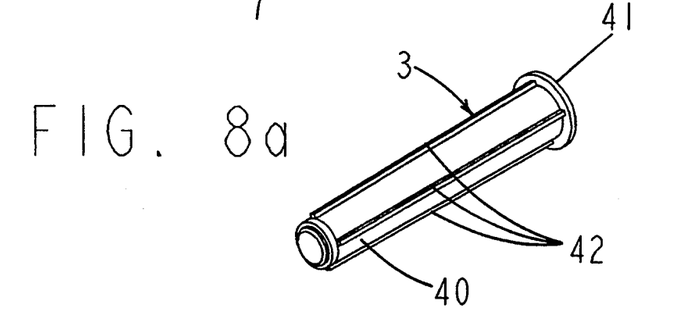
FIGS. 8a, 8b, & 8c are perspective views of the needle protective cap.
Figure 8B:
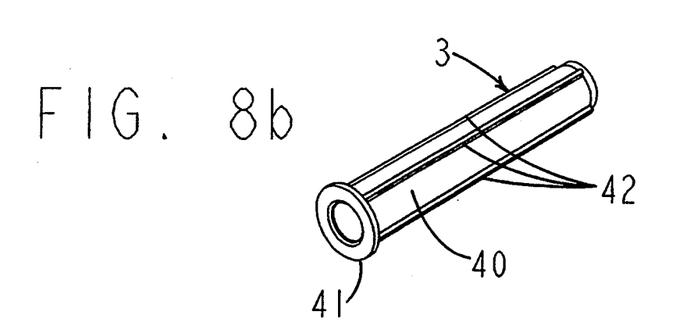
Figure 8C:
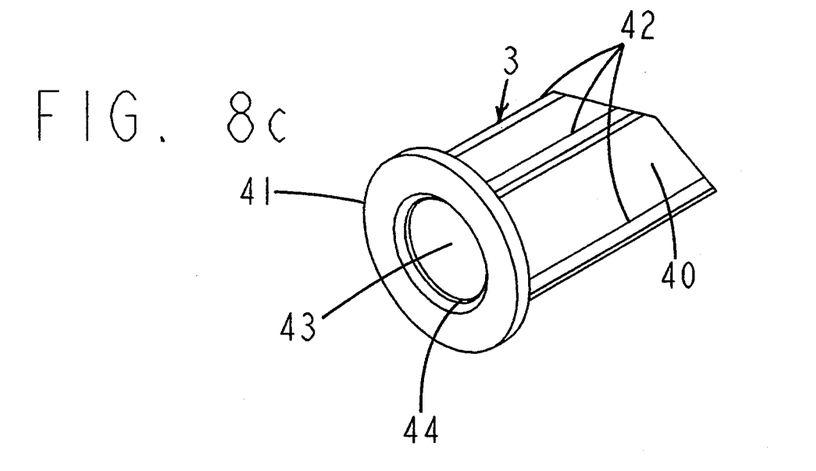
Figure 9A:
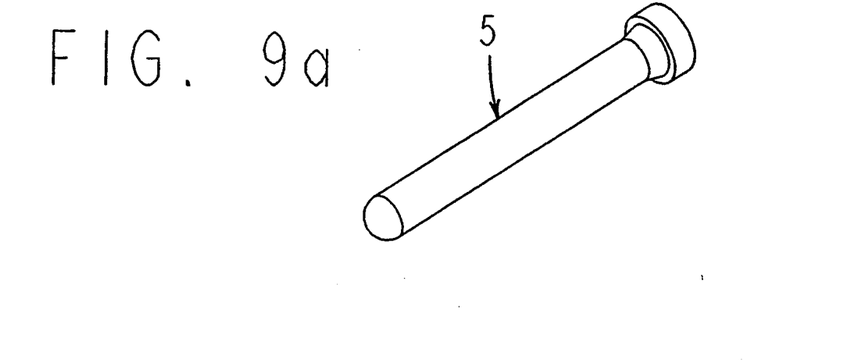
FIGS. 9a & 9b are perspective views of the needle boot.
Figure 9B:
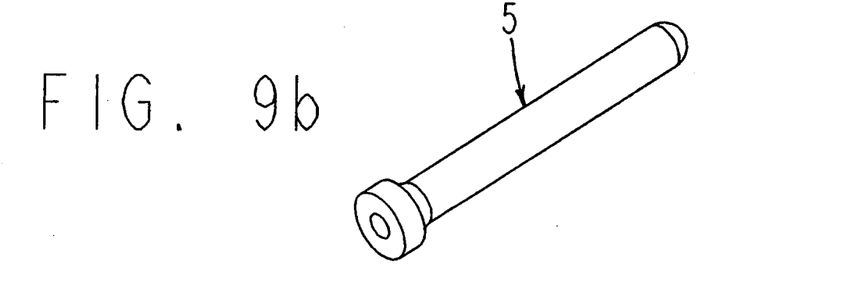

Referring to FIGS. 8a, 8b, & 8c, the needle protective cap 3 has a tapered section 40 with a ring 41 on its rear end. The tapered section 40 is closed at the forward end and has axial ribs 42 on its exterior surface. The ring 41 extends radially from the longitudinal axis of the needle protective cap 3 and provides a means of stripping and indexing in the manufacturing process. The inside surface 43 is parallel to the longitudinal axis of the needle protective cap 3 for a distance approximately equal to or greater than the length of the forward edges 22 (FIG. 5) of the needle support vanes 19 (FIG. 5). On the rear end of the interior surface 43 there is a raised ring 44 of slightly smaller diameter which provides an interference fit with the forward edges 22 (FIG. 5) of the needle hub support vanes 19 (FIG. 5). This ring 44 enhances the attachment of the needle protective cap 3 to the needle hub support vanes 19 (FIG. 5) and also assists in stripping the molds in the manufacturing process.

DESCRIPTION OF THE ASSEMBLY AND OPERATION OF THE PREFERRED EMBODIMENT

The device is fully assembled at the manufacturing facility. The assembled device of FIG. 1 is placed in a thermoform plastic tray (not shown) and sealed with lidding material. The packaged devices are then sterilized by gamma radiation and shipped to the end user (either directly or through a distribution chain).

Immediately prior to use, the lidding is removed and the assembly of FIG. 1 is removed from the tray. The needle protective cap 3 is then removed and the needle 4 (FIG. 2) inserted into the blood vessel of the patient. The needle boot 5 (FIG. 4a) prevents the blood from flowing into the cavity 14 of the device. A conventional evacuated blood collection tube 9 (FIG. 10) is then inserted into the cavity 14 of the device and pushed forward over the interior end 6 of the needle 4. This forces the needle end 6 through the needle boot 5 and the rubber stopper 50 (FIG. 10) of the blood collection tube 9 and into the evacuated interior of the blood collection tube 9. Blood is forced by intravenous pressure into the evacuated blood collection tube 9. When the desired amount of blood has entered the tube 9, the tube is withdrawn. Additional blood collection tubes are filled in this manner until the desired number of samples have been collected.

When the collection process has been completed, the short cylindrical section 30 (FIG. 3b) of the protector case 2 is held against the arm of the patient by gentle pressure with the index finger, and the body section 1 and needle 4 are pulled backward with the thumb and middle finger. The body 1 and needle 4 are withdrawn into the protector case 2 until the needle tip 7 is covered by the guard cylinder 32 of the protector case 2 and the detents 35 of the protector case detent arms 34 have engaged the slots 11 in the walls 12 of the channels 10 of the body 1. The entire device is then disposed of in an appropriate manner, without further exposure of the needle or other action required.

BRIEF DESCRIPTION OF THE FEATURES OF THE SYRINGE

The improvements which are the subject of this application relate to:
1. A modified cross-sectional shape of the body 1 which retains a rectangular shape of the body/protector case interface while permitting the body 1 to be molded to permit insertion of an evacuated blood collection tube 9 into the interior cavity 14.
2. A modified configuration of the detents 35 and detent pockets 11 which permits the protector case 2 to be locked in the guarded position by action of the detents 35 and slots (pockets) 11.
3. A modified configuration of the body 11 which includes windows 15 in the sidewalls 12 of the body 1 which permit insertion of the detent arms 34 into the body during assembly, and molding of the needle boot hub 21 in the interior of the body 1.
4. An arrangement to permanently affix a needle 4 to the body 1 which has a structure 21 which facilitates the molding of the body 1 and helps maintain high production rates by providing adequate cooling.
5. An arrangement to removably attach a needle protective cap 3 for covering the needle 4 prior to use.
6. A configuration of the short cylindrical section of the protector case which allows one handed retraction of the needle from the patient into the protector case.

What is claimed is:

1. A disposable blood collection tube holder comprising a body having a first forward end with a needle for penetrating a blood vessel of a patient and a second rearward end having a cavity for receiving an evacuated blood collection tube,
   a protector case adapted to slidably fit with respect to the body, and having a first open end through which the needle may extend and a second end wherein the second end of the of the case and the body have cooperating detent arms and channels with slots for facilitating placement of the case with respect to the body for uncovering and covering, respectively, an exposed end of the needle, and
   a needle hub molded integrally to the first end of the body to which the needle is attached.
2. A disposable blood collection tube holder as in claim 1 wherein the device has a needle protective cap removably attached to the body which covers the needle prior to use.
3. A disposable blood collection tube holder as in claim 1 wherein the body and protector case are both injection molded from plastic.
4. A disposable blood collection tube holder as in claim 2 wherein the needle protective cap is injection molded from plastic.
5. A disposable blood collection tube holder as in claim 2 wherein the protector case has a guard cylinder with slots projecting radially through the guard cylinder, and the body has needle hub support vanes at a first end which fit through the slots in the guard cylinder when the protector case is in a rearward (unguarded position), and
   the needle cap is removably attached to the body by interaction of an interior surface of the needle protective cap with forward edges of the needle hub support vanes.

6. A disposable blood collection tube holder comprising a body having a first forward end with a needle for penetrating the blood vessel of a patient and a second rearward end having a cavity for receiving an evacuated blood collection tube,
   a protector case adapted to slidably fit on the body, and having a first open end through which the needle may extend and a second end wherein the second end of the of the case and the body have cooperating detents and slots for facilitating placement of the case with respect to the body for uncovering and covering, respectively, an exposed end of the needle, and
   a needle hub molded integrally to the first end of the body to which the needle is attached, and
   detent arms molded to said second end of the protector case which extend rearward and slidably fit into channels formed into sides of the body.

7. A disposable blood collection tube holder as in claim 6 wherein the detent arms are molded at an outward angle from the axis of the protector case to provide an outward force by the detent arms on the wall of the channels of the body when the protector case is slidably fitted to the body.

8. A disposable blood collection tube holder as in claim 6 wherein the detent arms have outwardly extending detents molded to the ends of the arms which engage slots in the walls of the body to prevent axial movement of the protector case relative to the body when the detents are engaged with the slots.

9. A disposable blood collection tube holder as in claim 6 wherein the body has windows in the forward end of the channels which permit assembly of the protector case to the body and molding of a needle boot hub.

10. A disposable blood collection tube holder as in claim 6 wherein the detent arms include detents, and the body has a flared area at the second rearward end of the body to strengthen the cavity end of the body and provide a recess for the detents and a sloped ramp to force the detents inward into the channels within the body as the protector case is slid forward with respect to the body.

11. A disposable blood collection tube holder as in claim 1 wherein the protector case has a short cylindrical section of an outer diameter larger than the outer diameter of the body which permits the protector case to be held against the patient's body with one finger of a user's hand while the needle of the blood collection tube holder is retracted into the protector case with the same hand.

12. A method of holding the short cylindrical section of the protector case of the blood collection tube holder of claim 11 against the patient's body with the index finger while the body and needle of the blood collection tube holder are withdrawn with the thumb and middle finger of the same hand until the needle is covered by the protector case and the detents are engaged in the slots.

* * * * *